United States Patent [19]

Walker

[11] 4,158,920
[45] Jun. 26, 1979

[54] METHOD AND APPARATUS FOR TESTING FOR BRAIN DYSFUNCTION IN A HUMAN

[76] Inventor: Norman K. Walker, 6613 Sulky La., Rockville, Md. 20852

[21] Appl. No.: 771,387

[22] Filed: Feb. 23, 1977

[51] Int. Cl.² ............................................. G09B 19/00
[52] U.S. Cl. ..................................................... 35/22 R
[58] Field of Search ............. 35/22 R; 128/2 R, 2.1 R

[56] References Cited

U.S. PATENT DOCUMENTS

| | | | |
|---|---|---|---|
| 2,023,488 | 12/1935 | Poppen | 35/22 R X |
| 2,341,678 | 2/1944 | Wickes | 35/22 R X |
| 3,357,115 | 12/1967 | Kelley | 35/22 R |
| 3,579,865 | 5/1971 | Walker | 35/22 R |
| 3,792,464 | 2/1974 | Hameda et al. | 340/324 AD |
| 4,006,898 | 2/1977 | Greaf et al. | 273/85 R |
| 4,028,819 | 6/1977 | Walker | 35/22 R |

OTHER PUBLICATIONS

Applications Manual for Philbrick Octal Plug-In Computing Amplifiers, GAP/R K2 Series, p. 12, Title page, © 1956.
Zero Input Tracking Analyzer (ZITA Vb) and Auditory Discrimination Task (ADT Vb), Operating Instructions and Calibrations, Title Page, pp. i, ii, 1-13, Jul., 1971.
Linear Integrated Circuits, pp. i, ii and 2-4.

Primary Examiner—William H. Grieb
Attorney, Agent, or Firm—Larson, Taylor and Hinds

[57] ABSTRACT

A method and apparatus are presented for testing a human operator, and in particular a small child, for brain dysfunction, which method and apparatus require the human operator to perform a primary task which includes centering a spot of light on a reference point by rapidly moving a control stick back and forth. The primary task is provided by a Zero Input Tracking Analyzer (ZITA) unit that has no initial input and automatically nulls the operator's error, from his previous attempt to center the spot, with each subsequent attempt. In order to make more prominent any evidence of brain dysfunction, a secondary task is provided by an Auxiliary Distraction Task (ADT) unit which produces a "distraction stress" while the operator is carrying out the primary task. This task requires the human operator to respond to the stimuli of high or low tones, presented to him by headphones, by moving another control stick forward or backward for the high and low pitches, respectively. A common display/recorder is used to record the performance on both tasks. Brain dysfunctions, including brain seizures, epilepsy, and hyperactivity, is evidenced by a slowness in response to the tasks, or complete non-responsiveness, due to very short lapses of consciousness or attention, which are characteristic of brain dysfunction.

13 Claims, 7 Drawing Figures

ZITA TASK WITHOUT ADT STRESS ("O")

VERY GOOD RESPONSE

AVERAGE RESPONSE
(FOR SUB-TEENS)

SLOW RESPONSE

RESPONSE WITH SEIZURES

ZITA TASK WITH ADT STRESS ("Os")

AVERAGE RESPONSE

RESPONSE WITH SEIZURES
(HYPERACTIVE)

METHOD AND APPARATUS FOR TESTING FOR BRAIN DYSFUNCTION IN A HUMAN

BACKGROUND OF THE INVENTION

1. Field of the Invention

This invention relates to improvements in physchological testing methods, and in particular to a method and apparatus for testing for brain dysfunctions in a human, and in particular a small child.

2. Description of the Prior Art

A number of methods and apparatus are disclosed in the prior art that are useful for performing physiological tests on individuals. Such methods and devices are disclosed in U.S. Pat. Nos. 3,357,115 (Kelley), 2,341,678 (Wickes), and 2,023,488 (Poppen). These methods and apparatus are generally designed to determine if the individual is suited to a particularly stressful occupation, which occupation involves responding correctly to a multitude of varied stimuli. Occupations which can be particularly stressful include, for example, those held by air traffic controllers, airplane pilots, astronauts, and submarine crew members.

These methods and devices, however, are not particularly helpful for testing for brain dysfunctions in children ranging in age from the very young to the subteens, for the following reasons. First, these tests are inherently complicated as they attempt to duplicate the complicated and stressful environment of the occupation. Thus, it is usually difficult to teach a child how to take the test, let alone expect the child to accurately respond to the stimuli provided thereby. Second these tests generally measure the persons ability to coordinate a variety of physiological factors, such as for example simple reaction time and visual perception, as would be required of an applicant for the aforementioned occupations. Thus the results of such tests would not distinguish between brain dysfunction (as tested by response time) and visual impairments.

Another prior art device, which includes more simply learned tasks and thus is more suited to testing children is disclosed in U.S. Pat. No. 3,579,865, issued to Norman K. Walker, the present applicant, said patent being incorporated herewith. The patent discloses a method and apparatus for measuring the effect of stress on the performance of a primary task while a secondary task is also provided to be performed by the human operator. The primary task (Zero Input Tracking Analyzer or ZITA) involves the use of a control stick to keep a light spot centered on a reference point. The control stick in one embodiment of that device has two positions, one position causing the light spot to travel to the left of the reference point, at a constant velocity, and the other position causing the light spot to travel to the right of the reference point at a constant rate. Velocity, acceleration, lag and/or lead functions can be selected to make the light spot travel at other than a constant velocity and thus make the centering task more difficult. As the control stick is always in one of the two positions, when the device is actuated, the light spot will automatically start traveling away from the reference point. Consequently, no initial input is needed and the human operator has only to null his own error from his previous response, i.e., center the light spot on the reference point.

The secondary task (Auxiliary Distraction Task or ADT) produces a "distraction stress" to the human operator while he is carrying out the primary task. This task requires that the human operator respond to the stimuli of high or low tones, presented to him by headphones, by moving another control stick forward or backward between two positions, for the high and low tones, respectively. Alternatively the operator could press push buttons to respond to the stimuli. A common display/recorder is used to record the performance on both tasks for analysis.

Studies have shown, however, that very small children do not have what can be described as a "center concept". This is to say, if a small child is asked to hold a dot of light in the center of a screen or on a reference point, the child will find to his delight that the spot of light will obey the commands of the control stick. The child can steer the light spot, but generally has no motivation to hold the spot on a reference point.

Further, the test results of the method and apparatus disclosed in this patent include a visual perception factor (following the spot of light with the eye) which can cloud evidence of some brain dysfunctions.

SUMMARY OF THE INVENTION

The present invention provides for a method and an apparatus for testing for brain dysfunction in humans, and especially in small children, that overcomes the disadvantages of the prior art devices. The method of the invention comprises the steps of providing a movable and visible tracking spot and a reference position therefor; instructing the human operator to hold the tracking spot on the reference position; causing movement of the spot solely in response to control commands from the human operator, a first control command for initially aligning the tracking spot with the reference position and then for allowing the tracking spot to move away from the reference position in a first direction, and a second control command for initially aligning the tracking spot with the reference position and then for allowing the tracking spot to move away from the reference position in a second direction, which second direction is opposite the first direction; and recording the movements of the tracking spot for analysis.

A further aspect of the method of the invention includes the steps of providing an auxiliary stimulus; requiring the human operator to respond to the auxiliary stimulus; and recording the response for analysis. In a preferred embodiment, the auxiliary stimulus includes at least two different tones, and/or lights, a different operator response required for each tone.

This method does overcome the disadvantages of the prior art in that first the tasks provided can simply and easily be taught to young children, so that any results obtained are not clouded by the possibility that the child does not understand the tasks. Second, the method provides for the initial aligning of the tracking spot with the reference position with each control command. Thus the method automatically "centers" the tracking spot for the child. Third, and following directly from the second point, though the child is instructed to keep the tracking light centered on the reference position, visual perception is not a factor present in the test results as the tracking spot does automatically center itself with each control command. Thus the results can give an unclouded indication of periods of temporary unconsciousness as evidenced by slow responses or no response at all, such periods of unconsciousness potentially indicating brain dysfunction.

A further aspect of the method of the invention eliminates the use of the tracking spot and reference position.

The human operator or child is instructed to continuously move a control stick between two positions as quickly as possible. The movement of the control is recorded and can give an indication of brain dysfunctions. Auxiliary stimuli can be provided to increase the stress on the human operator, and to investigate the time taken to switch attention from the main task and back. An excessive delay indicates a second form of brain dysfunction.

In accordance with the preferred embodiment of the invention an apparatus is provided comprising a display for displaying a reference position, and a movable and visible tracking spot. The apparatus further includes a control for controlling the movement of the tracking spot, the control including a control stick having at least a first position and a second position. The first position of the control stick is for initially aligning the tracking spot with the reference position and then for allowing the tracking spot to move away from the reference position in a first direction. The second position of the control stick is for initially aligning the tracking spot with the reference position and then for allowing the tracking spot to move away from the reference position in a second direction, opposite to the first direction. The apparatus further includes a recorder for recording the movement of the tracking spot.

An aspect of the apparatus includes an auxiliary stimulus device for providing a distracting stress to the human operator.

In another embodiment of the invention, the display, including reference position and tracking spot, is eliminated, and the operator's ability to rapidly and regularly move the control stick between the first position and the second position is recorded and analyzed for evidence of brain dysfunction.

Additional features and advantages of the invention will be set forth in, or apparent from, the detailed description of a preferred embodiment found hereinbelow.

DETAILED DESCRIPTION OF THE PREFERRED EMBODIMENT

Figure 1:
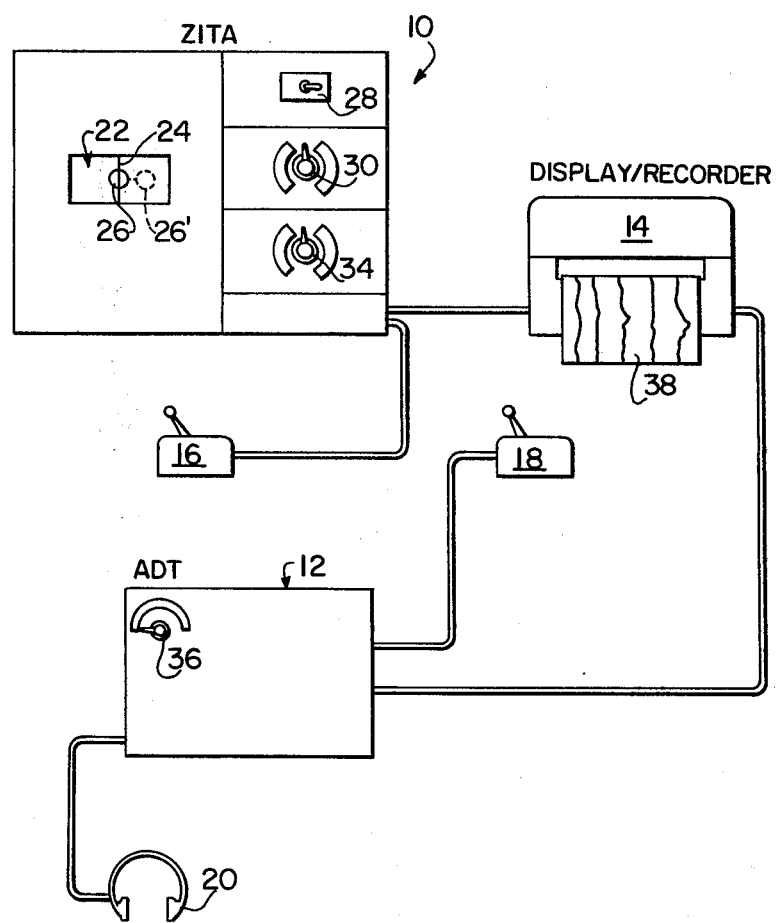
FIG. 1 is a schematic diagram of the apparatus of the invention.

With reference to FIG. 1, there is depicted apparatus of the invention. The apparatus include a ZITA Unit 10, an ADT Unit 12, and a display/recorder 14. A control unit 16 is manipulatable by the test subject with his dominant hand to perform a tracking task on the ZITA unit, while control unit 18 is manipulatable with the other hand in response to the stimuli from the ADT unit. Depending on the preference of the test subject, the positions of control units 16 and 18 can be reversed, if for example the test subject would rather perform the tracking task with the left hand. Although shown as separate units, it is to be understood that ZITA Unit 10, ADT Unit 12, and display/recorder 14 can be combined into a compact, portable assemblage (not shown).

ZITA Unit 10 is a fully digital unit and contains all the necessary equipment to carry out the primary task, which is a tracking task. A screen 22 is the visual presentation to the human operator or test subject, with a grid line 24 in the center thereof to provide a control or reference position. A light spot 26 is movable in one dimension across screen 22 and controlled by the test subject via control unit 16. The test subject can manipulate the control stick of control unit 16 to the right, light spot 26 responding by initially centering itself on grid line 24 and then moving to the right at a constant velocity. Light spot 26', shown in broken lines, depicts movement of spot 26 to the right. The test subject can manipulate the control stick of control unit 16 to the left, light spot 26 responding by initially jumping from position 26' and centering itself on grid line 24, and then moving to the left at a constant velocity. The electronic circuitry necessary to provide a tracking spot responsive to a control as described hereinabove is well known in the art.

In this preferred embodiment, control unit 16 is a two position "switch-type" or "bang-bang" control unit. However, as disclosed in U.S. Pat. No. 3,579,865, control unit 16 can be a three position or a proportional control unit and switch 28 and controls 30 and 34 can vary the response of light spot 26 to control unit 16 by, for example, converting control unit 16 from a two to a three position controller, and by introducing non-centering-constant-velocity, acceleration, lag and/or lead functions. For purposes of identification, the task of the preferred embodiment which includes automatic centering of light spot 26 is presently referred to as "TASK-0". For completeness, though not presently necessary for this discussion, the task with a non-centering-constant-velocity function is referred to as "TASK 1", the task with the acceleration function "TASK 2", and the task with the lag or lead function "TASK 3".

ADT unit 12 is principally a sound generator producing two sounds, consisting of a "ping" and a "pong", which are the auxiliary or secondary stimuli presented to the test subject. The "ping" denotes a short pulse of high pitch sound, while the "pong" denotes an equal length pulse of a low pitch sound. These sounds are presented to the test subject by headphones 20. Since some children have difficulty in distinguishing between tones, two lights are also provided (described in another U.S. Pat. No. 4,028,819, issued June 14, 1977 to the present inventor), the "ping" light to the right of the reference mark, the "pong" on the left. The test subject is provided with control unit 18 for the ADT, which requires him to move the control stick thereof, either forward or backward, depending upon which of the sounds have been designated forward or backward. The stimuli of ADT 12 are presented in a random order, but at predetermined intervals, which intervals can be set by internal program means such as switch 36. The ADT can normally be set for an interval of 2 seconds between stimuli, but other intervals are also used.

The display/recorder 14 can be any one of a number of commercially available units that provides a graph type record 38. The movement of light spot 26 and the response to the ADT stimuli are recorded thereon.

The operation of the above disclosed apparatus in accordance with the method is as follows. Initially only ZITA unit 10 is used and the test subject is shown how light spot 26 responds to control unit 16. The test subject (usually a child of four, though this method and apparatus is effective for operators ranging in age to the subteens and beyond, to any age, if the operator has problems learning a more difficult task) is then given instructions such as "We want you to hold the spot of light in the center. All you have to do is hold the control lightly and jiggle it back and forth as quickly as you can." ZITA unit 10 is then switched on, and as control unit 16 is always in one of two positions, light spot 26 is initially centered and immediately begins to move to the right or left.

As the spot of light is automatically centered with each change of position of the control stick of control 16, the visual perception of the test subject in centering the light spot is not a measured factor. The test measures a motor function more basic even than simple reaction time. The light spot display, however, helps to retain the test subject's interest, and is an essential part of "TASK 1", also used.

Figure 2:
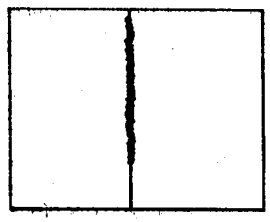
FIG. 2 to FIG. 7 depicts test data obtained using the apparatus of the invention.
Figure 3:

Referring to FIGS. 2 to 5, results of several "TASK-0" test are depicted. FIG. 2 depicts a very good response where the test subject is moving the control stick rapidly and regularly, back and forth. FIG. 3 represents an average response for a sub-teenage person, the spot of light, as evidenced by the graph, not being quite as tightly held on the reference position.

Figure 4:
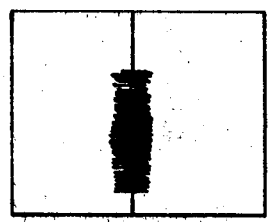

FIG. 4 depicts a slow response to "TASK 0". A slow response is defined by a slow "jiggling" of the control stick, and is evidenced by a large amplitude in the movement of the light spot from the reference position, as depicted by the graph. The child or test subject is moving the stick steadily, but slowly. Such children are sometimes mentally retarded or hypokenetic, have cerebral palsy, or are slow for some other reason.

Figure 5:
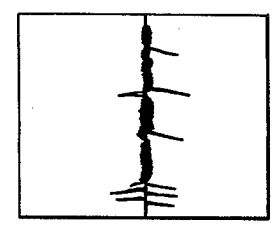

FIG. 5 depicts a response that identifies potentially abnormal brain functioning. The spikes from the graph represent periods of up to half a second and more when the "jiggling" activity ceases due to, in some cases, very short lapses of consciousness, due to seizures or epilepsy. This then represents some evidence of brain dysfunction.

It is to be understood that the area under all of the above referenced graphs can be summed or integrated to derive an absolute error score. Such scores can then be compared among themselves.

Figure 6:
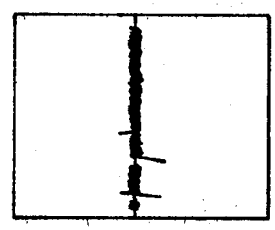

If the task of ADT unit 12 is added to the task of ZITA unit 10 (the new task denoted "TASK 0s") additional "stress" is placed on the child. If the child is not easily distracted, there is little change in the display readout. Comparing FIG. 3 with FIG. 6 (FIG. 3 representing only the ZITA unit response), the graphs are essentially the same except for a couple of small spikes.

Figure 7:
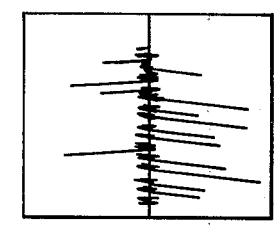

On the other hand, if a hyperactive or easily distracted child is tested, each time he responds to the ADT stimuli, the child forgets about the ZITA unit, the motion of the stick control of the ZITA unit ceases, and a spike is recorded (FIG. 7). Thus a child who is hyperactive, or prone to seizures resulting in lapses of consciousness, is easily identified.

In an alternate embodiment (not shown) of the apparatus of the invention, the light spot and reference positions are eliminated and the test subject is just asked to jiggle a control stick. The response is recorded and analyzed in a manner similar to that discussed hereinabove.

In another alternable embodiment (not shown) of apparatus of the invention, the ZITA unit comprises an analog device including an integrator shunted by a resistor. Thus, unlike the digital ZITA unit 10 disclosed hereinabove, where the light spot automatically homes to the reference position with each reversal of movement of the control stick, with the analog unit, the light spot homes to a position which is slightly offset, representing a measure of stick voltage output. From this position, the light spot moves at a steady rate as before. This produces a slightly different looking display output, but the net result is the same, and the area under the graph or integrated absolute error can be used to interpret the results. Alternatively, a third switch can be provided between the two control switches to momentarily short circuit the integrator and home the light spot.

It is to be understood that the ADT unit can be supplemented or replaced by other stimuli producing units, as for example a unit that provides light flashes of differing colors and/or tactile stimuli.

Alternate methods of using the above disclosed devices can include timing the interval between stick movement and detecting those which exceed the average by some definite margin and then counting or summing the time intervals detected. Display/recorder 14 can be modified to accomplish this function.

Although the present invention has been described relative to an exemplary embodiment thereof, modifications and variations can be effected in these embodiments without departing from the scope and spirit of the invention.

I claim:

1. A method for testing a human operator for brain dysfunction comprising the steps of:
   providing a movable and visible tracking spot and a reference position therefor;
   causing movement of the spot solely in response to control commands initiated by the human operator including initially aligning the tracking spot with the reference position when a first control command is initiated by the operator and then causing the tracking spot to move away from the reference position in a first direction, initially aligning the tracking spot with the reference position when a second control command is initiated by the operator and then causing the tracking spot to move away from the reference position in a second direction; and
   recording the movements of the tracking spot for analysis.

2. A method in accordance with claim 1 wherein the control commands are provided by a controller having a two position control stick, the method including the steps of moving the control stick to a first position to initiate the first control command and moving the control stick to a second position to initiate the second control command.

3. A method in accordance with claim 2 wherein the control stick is moved back and forth between the first position and the second position as rapidly as possible.

4. A method in accordance with claim 2 including causing the movement of the spot in the direction of the movement of the control stick.

5. A method in accordance with claim 1 including the steps of providing an auditory stimuli of at least two different tones;
   supplying a different control response from the human operator for each tone;
   varying the order of presentation of the tones; and
   recording the different control responses for analysis.

6. A method in accordance with claim 1 including the steps of:
   providing an auxiliary stimulus;
   requiring the human operator to respond to the auxiliary stimulus; and
   recording the response for analysis.

7. A method in accordance with claim 1 including the steps of:

providing the first control command for substantially, instantaneously and initially aligning the tracking spot with the reference position and then for allowing the tracking spot to move away from the reference position at a constant velocity in the first direction; and providing the second control command for substantially, instantaneously and initially aligning the tracking spot with the reference position and then for allowing the tracking spot to move away from the reference position at a constant velocity in the second direction, which second direction is opposite from the first direction.

8. A method in accordance with claim 1 further including the steps of summing the area under a graph representing the record of the movement of the tracking spot.

9. A method in accordance with claim 2 further including the steps of timing the time interval between movements of the control stick; detecting the time intervals that exceed a preselected minimum time interval; and counting or accumulating the detected time intervals.

10. A method for testing a human operator for brain dysfunction with an apparatus including a controller having a two-position control stick comprising the steps of:

the human operator moving the control stick between the two positions as quickly as possible; and recording the movement of the control stick for analysis with a recording means as follows:

initializing the recording means when the control stick is moved to one position; and then causing the recording means to track in a first direction; and initializing the recording means when the control stick is moved to the other position and then causing the recording means to track in a second direction.

11. A method in accordance with claim 10 including the steps of:

providing an auxiliary stimulus;

requiring the human operator to respond to the auxiliary stimulus; and recording the response for analysis.

12. A method in accordance with claim 10 including the steps of providing an auditory stimuli of at least two different tones;

supplying a different control response from the human operator for each tone;

varying the order of presentation of the tones; and recording the different control responses for analysis.

13. A method for testing a human operator as claimed in claim 10 wherein said recording means provides a record and said recording means is initialized by substantially instantaneously aligning said recording means with a reference position when said control stick is moved to either the first or the second direction.

* * * * *